United States Patent [19]

Lustig et al.

[11] 4,321,041
[45] Mar. 23, 1982

[54] MINIATURIZED CONTRA-ANGLE

[75] Inventors: Leopold P. Lustig, 304 Greenwood St., Newton Centre, Mass. 02159; Anselm Yaron, Brookline, Mass.

[73] Assignee: Leopold Paul Lustig, Newton, Mass.

[21] Appl. No.: 209,877

[22] Filed: Nov. 24, 1980

[51] Int. Cl.³ .......................... A61C 1/12; A61C 3/02
[52] U.S. Cl. ................................................. 433/133
[58] Field of Search ............... 433/133, 114, 124, 165; 408/126, 226

[56] References Cited

U.S. PATENT DOCUMENTS 3,368,279  2/1968  Weissman .......................... 433/133

Primary Examiner—Robert Peshock
Attorney, Agent, or Firm—Alfred H. Rosen

[57] ABSTRACT

A dental hand-piece of the type known as "contra-angle" uses a pair of helical gears on shafts that rotate on respective axes which pass by each other but do not intersect. The gears, one set of which is on a tool driver and the other set of which may be formed in the shaft of a dental tool, engage in respective pitch circles, the diameters of which are smaller than their respective outer diameters.

17 Claims, 5 Drawing Figures

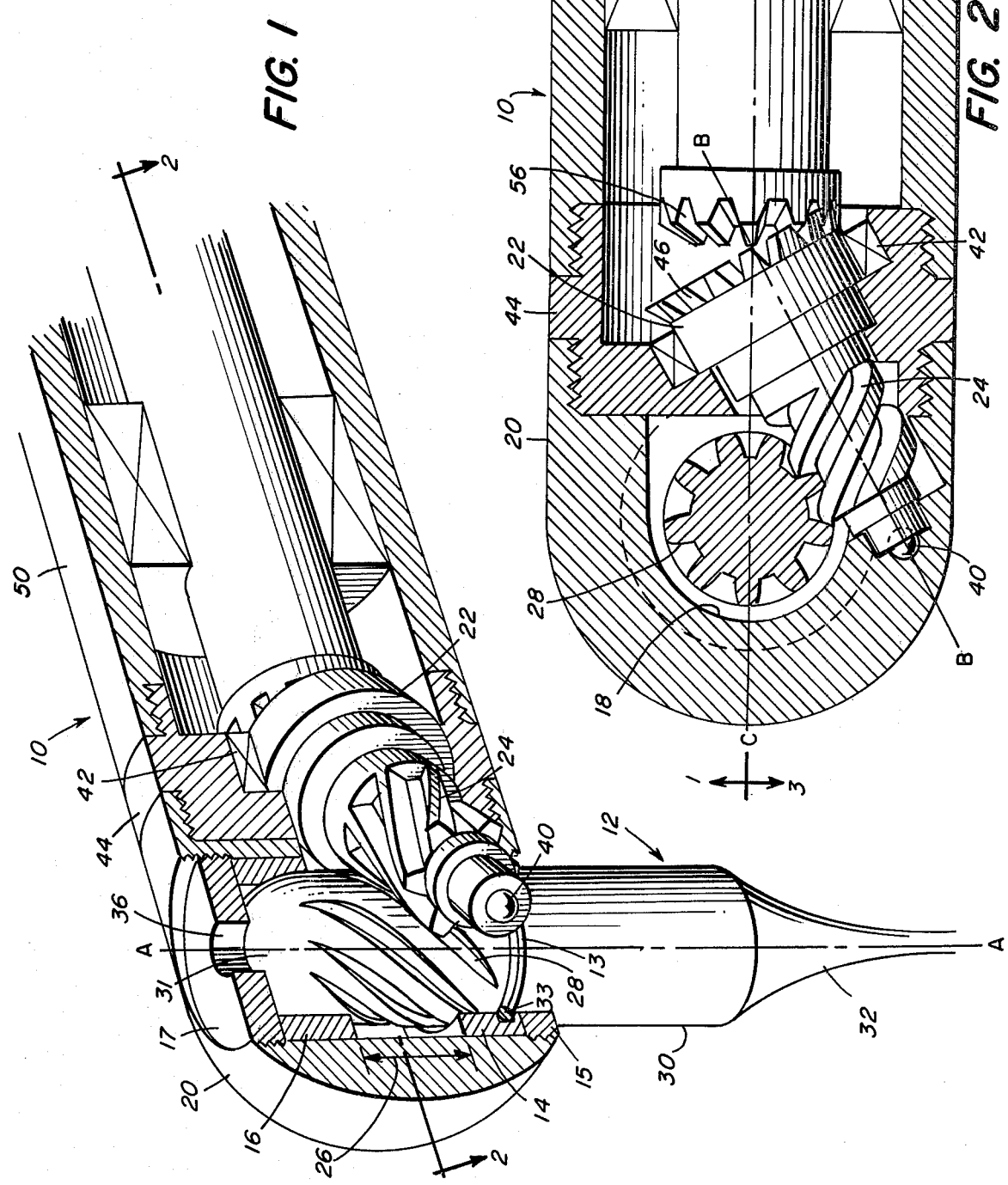

MINIATURIZED CONTRA-ANGLE

INTRODUCTION

This invention relates to contra-angle type operator mechanisms for rotatable tools, such as those used in dentistry. A principal purpose of the invention is to provide a new structural design of such contra-angle type operator mechanisms which can be realized in smaller sizes than have heretofore been available. For example, where the typical dental contra-angle available today has a tool shaft holding socket which is 7 to 10 mm in height, and about 7 mm in outer diameter, the present invention can reduce those dimensions each to the range of 4 mm to 5 mm. This is highly desirable for use in small mouths, of children and many women, as well as for work such as pin-setting in dental reconstruction procedures, where it is vital that the dentist be able to see precisely where he is drilling a hole or setting a pin.

BACKGROUND OF THE INVENTION

Dental hand-pieces of the type known as "contra-angle" tool holders generally include an elongated tubular housing arranged to be coupled at one end to an enclosure for the drive mechanism of a dental motor and enclosing an aley for a drive shaft which couples to the drive mechanism. At the other end the drive shaft is coupled to a tool shaft, or to a tool clutch, through gears that rotate the tool on an axis transverse to the drive shaft axis, and a stub housing is provided to enclose the tool and the direction-changing gears. Typical of contra-angle tool holders, the stub-housing is provided with openings at both ends, one to receive the tool and the other to give access to mechanism to lock the tool in place. U.S. Pat. No. 3,369,298 shows one example of such contra-angle tool holders; in that example a clutch is permanently rotatably fixed in the stub-housing, and a tool can be removably inserted into the clutch from one end, while a lock mechanism is provided at the other end. In other examples of such contra-angles, the tool is inserted through the housing from the lock-end of the stub-housing, and a removable (e.g. threaded) cap is provided at the same end to perform the lock function. As contra-angles are made smaller, these parts, epecially removable caps, become so small that they are difficult to manipulate and are easily dropped to the floor, and sometimes lost.

An additional impediment to making contra-angles smaller derives from the direction-changing gears that are used in contra-angle hand-pieces of known designs. In some cases a crown gear drives a tool clutch through a ring of gear radially extending from and surrounding the outer side surface of the clutch; an example is shown in Kaltenbach U.S. Pat. No. 2,319,328. In other cases, bevel gears are used for direction changing, in which case the radially-extending bevel gears surround and extend from the outer side surface of the tool holder or clutch; an example of this case is shown in Flatland U.S. Pat. No. 4,053,983.

In a copending application of one of the present applicants and another, Ser. No. 970,468 filed Dec. 18, 1978, it is taught to affix the radially-extending bevel gear ring directly to the shaft of a tool. This improvement allows the elimination of a clutch component. However, room must be provided for a ring of radially-extending gears surrounding the tool shaft, and for some dentists the need to equip an operatory with a set of "no clutch" tools having their own drive gears, in addition to the already existing tools designed for holding in a clutch, may be objectionable.

GENERAL NATURE OF THE INVENTION

The present invention makes possible a significant and important reduction in the size of a dental contra-angle by employing for the direction-changing gears two sets of helical gears on respective axes which pass by each other but do not intersect each other. One set of the helical gears is on a tool driver; the other set may be on a clutch mechanism or on the shaft of a tool. In either event, the gears pass by each other, and engage in respective pitch circles the diameters of which are each smaller than their respective outer diameters. The outer diameter of the helical gears on a tool shaft can be the same as the outer diameter of a typical prior-art tool shaft which has no gears on it, in which case a tool having helical gears on it according to the invention can be used in a prior-art contra-angle clutch, as well as in the new contra-angle of the invention.

For holding such a tool according to the invention, the new contra-angle provides first and second tubuar guides, serving the function of, for example, friction-grip clutches, these guides being spaced apart collinearly in the tool space of the contra-angle, with an access space between them. The helical gears on the tool driver intersect the access space, where they can mesh with the helical gears on a tool shaft that is present, held rotatably between the two guides. If a clutch is permanently held between the two guides, which then could serve the function of its anti-friction bearings, the helical gears on the clutch would again not be required to project beyond the normal outer diameter of the clutch mechanism. However, according to a preferred embodiment of the invention, the greatest reduction in size of a contra-angle is made possible by forming one set of helical gears directly on the shaft of a dental tool. Two versions of the preferred embodiment are illustrated in the drawings which accompany this application.

BRIEF DESCRIPTION OF THE DRAWINGS

FIG. 1 is a longitudinal side-sectional view of a contra-angle according to the invention, showing a tool in the tool socket, in cooperative relation with a tool driver, the latter two components being shown in full side view;

FIG. 2 is a section on line 2—2 of FIG. 1, in which the tool driver and the drive shaft are shown in full side view;

DETAILED DESCRIPTION OF THE DRAWINGS

Figure 3:
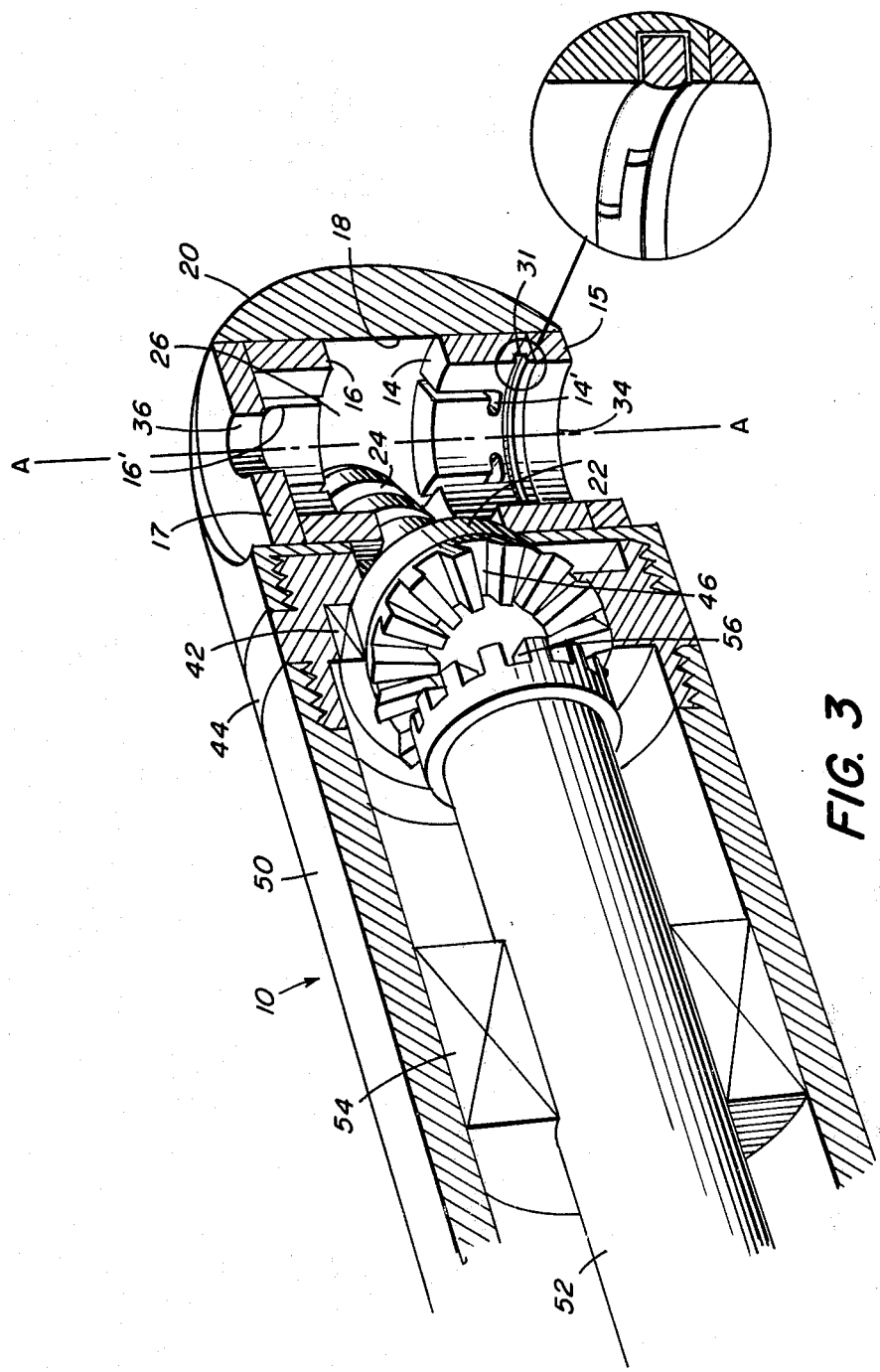
FIG. 3 is a longitudinal side-sectional view of the contra-angle shown in FIG. 1, taken from the opposite side, with the tool removed to show grip details of the tool holders.

FIGS. 1-3, inclusive, show a dental contra-angle 10 fitted with a rotatable tool 12. The tool is held in first and second tubular guides 14 and 16, respectively, which are spaced apart collinearly in a cylindrical bore 18 which extends on a first axis A—A in a first housing part 20. A tool driver 22 that is rotatable around a second axis B—B passing by but not intersecting the first axis A—A has a first set of helical gears 24 extending along the second axis and intersecting an access space 26 between the first and second tubular guides 14, 16. The tool 12 has a second set of helical gears 28 formed on its shaft 30, to one end of which a rotationally-working tool 32 (e.g: a dental drill or bur) is affixed. Uniquely, the second set of helical gears is formed in a tool shaft 30 of usual outer diameter. For example, if a tool shaft having an outer diameter of 1.6 mm is used, the outer diameter of the second set of helical gears is approximately 1.6 mm; in which case the diameter of the pitch circle may be approximately 1.3 mm, and the diameter of the root circle may be approximately 1.0 mm. Similarly, if the tool used has a shaft with a nominal outer diameter not exceeding approximately 2.30 mm, the second set of helical gears will have the same outer diameter. In this manner, the invention provides the possibility to enjoy its advantages with tools which can also be used in other contra-angles that do not provide the advantages of the invention.

When the tool 12 is present in the bore 18 it may be held, in a known manner, frictionally within the tubular guides 14, 16 which, for that purpose are fashioned as friction-grip clutch members, as is indicated by slots 14' and 16', respectively, in FIG. 3. The friction-grip guide members 14, 16 are held in the bore 18 by stops 15 and 17, respectively, threadedly engaged in the bore 18 as is illustrated in FIG. 1. The guide members 14, 16 may be held in place in the bore 18 in antifriction devices (not shown). The helical gear teeth of the second set 28 are carried toward the free end 31 of the shaft 30 which is first inserted into the bore 18 through an access opening 34 in the lower stop 15 when the tool is installed in the contra-angle, to facilitate engaging the second set of helical gears with the first set of helical gears 24 on the tool driver 22. A slight twisting of the tool shaft 30 around the axis A—A as the tool shaft passes through the access opening 34 is sufficient to engage the two sets of helical gears. The tool shaft is, in the limit, seated in the upper guide 15, in which posture the two sets of helical gears are engaged in the access space 26 between the first and second tubular guides 14 and 16, respectively. The tool 12 can be ejected from the bore 18 by a pin or rod pushed through a hole 36 in the upper stop 17.

The tool driver 22 is supported at a small end in the first housing part 20 by a ball bearing 40 and near the other larger end in an annular anti-friction bearing 42 which in turn is supported in a tubular joining member 44 between the first housing part 20 and a second housing part 50. A first crown gear 46 is fitted to the larger end of the tool driver. A drive shaft 52 rotatable on a third axis C—C is supported in an annular anti-friction bearing 54 within the second housing part 50. A second crown gear 56 fitted to the inner end of the drive shaft engages the first crown gears for driving the tool driver 22 from a dental engine (not shown) to which the drive shaft may be coupled in any of several known ways.

The direction of rotation of the tool driver 22 will normally produce a component a force parallel to the tool axis A—A tending to push the tool 12 toward the upper stop 17. In case of reversal of rotation of the tool driver, an oppositely directed force component tending to eject the tool from the bore 18, may be produced. An annular groove 13 (FIG. 1) is provided in the tool shaft 30, and a companion annular groove 31, (FIG. 3) is provided in the first tubular guide 14, in which a spring-form ring 33 can be carried, for engaging the groove 13 of the tool, for retaining the tool in place against such an oppositely-directed force.

Figure 4:
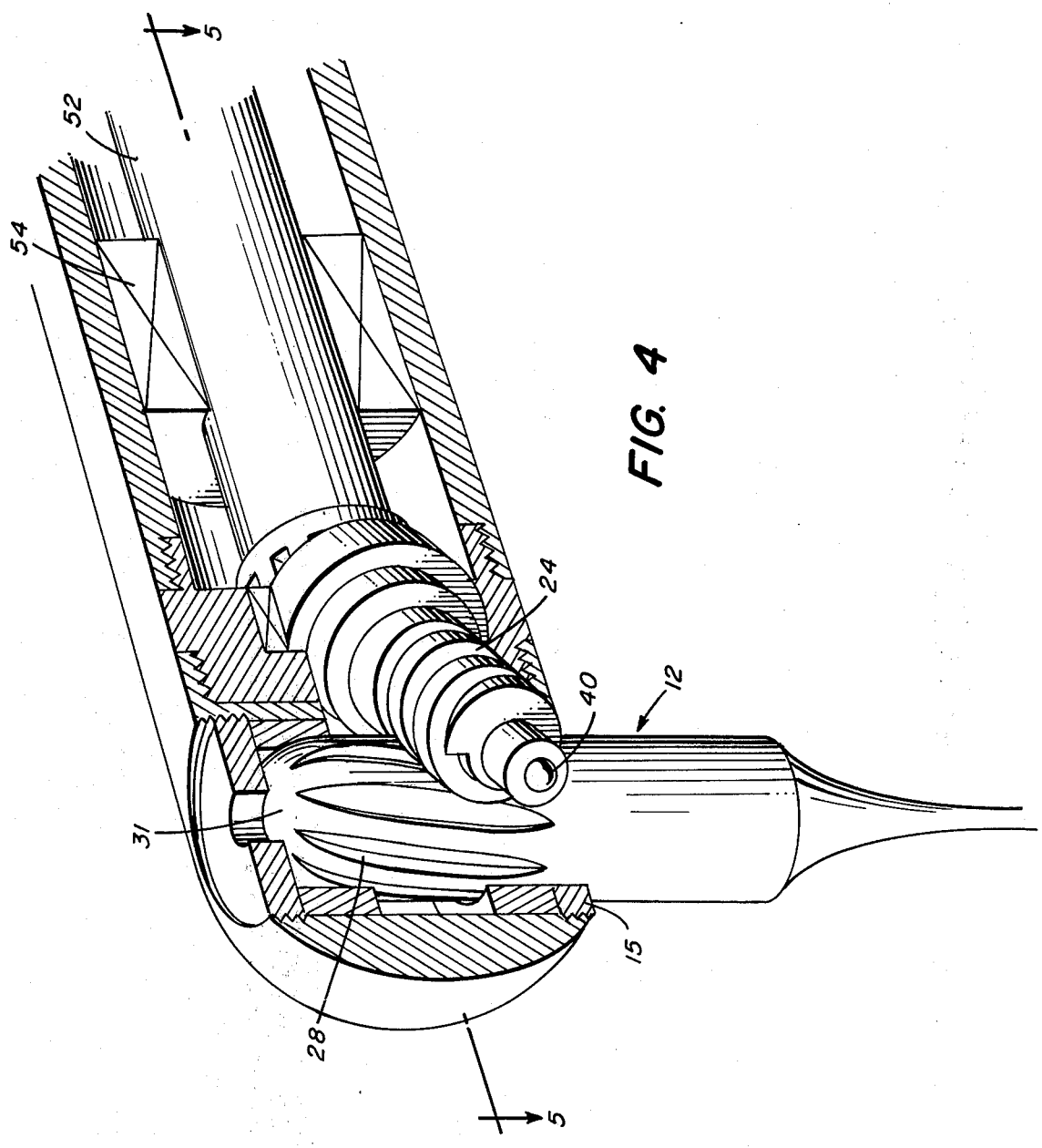
FIG. 4 is a longitudinal side-sectional view of an embodiment similar to FIG. 1 in which the helical gears have different helix angles.
Figure 5:
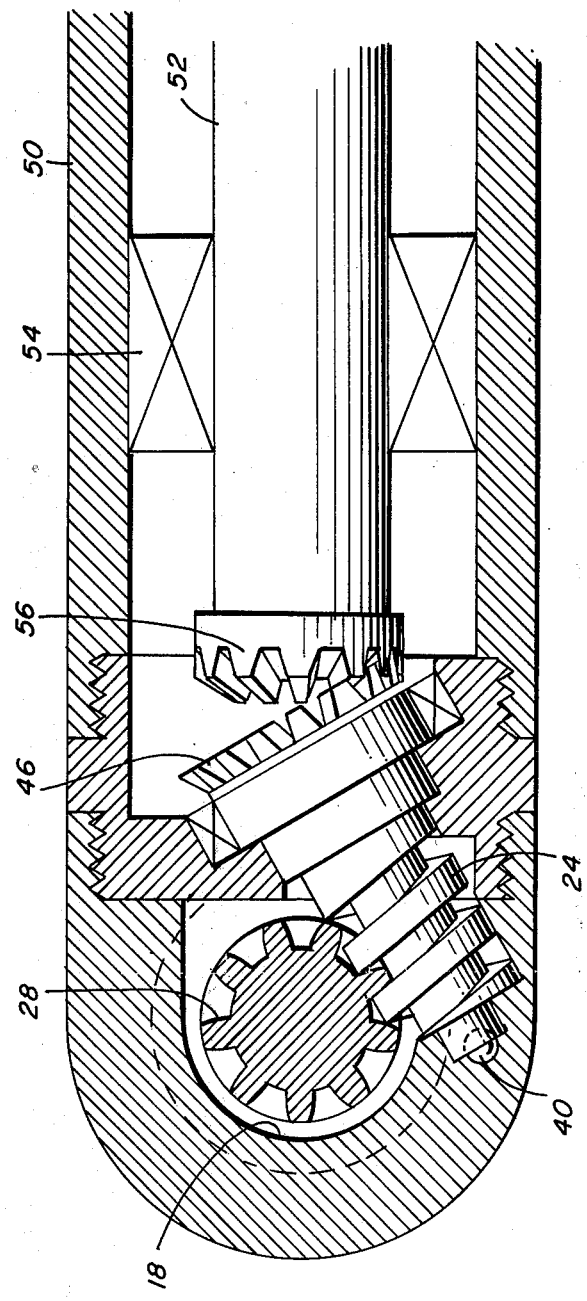
FIG. 5 is a section on line 5—5 of FIG. 4, showing the tool driver and drive shaft in full side view.

The helical gears 24 and 28 may have respective helix angles approximating 45° to the respective axes B—B of the tool driver 22 and A—A of the tool 12, as is shown in FIGS. 1–3. Alternatively the helix angles may range toward 90° to the axis B—B of the tool driver 22 (worm gear) and nearly 0° to the axis A—A of the tool 12, as is illustrated in FIGS. 4 and 5, which are otherwise similar to FIGS. 1–3. When the helical gears 24 and 28 have respective helix angles approximating 45° the turning ratio between the drive shaft 52 an the tool shaft gears 28 can be made equal or substantially equal to 1:1. On the other hand, when the tool-driver helical gear 24 approaches a worm gear the rotational speed of the tool 12 will be substantially less than the rotational speed of the tool driver 22.

The helical gears 28 of the second set on the tool shaft 30 are extended at least partially over a first end 31 of the shaft, for meshing the second set of helical gears with the first set 28 when a tool is inserted into the bore 18 through the access opening 34.

The tool axis A—A is illustrated in a perpendicular relation to the plane containing the tool driver axis B—B and the shaft axis C—C. The tool axis can be placed in a different angular relationship to that plane, or to the tool driver axis B—B, for example up to about 30 degrees off-perpendicular to one another, if desired.

The housing components 20 and 50, coupled with the joining member 42, together form a single unit having a substantially straight uniform exterior paralleling the drive shaft axis C—C. If the tool 12 is 1.6 mm in exterior diameter, the exterior diameter of the tubular housing 50 can be made as small as five millimeters.

We claim:

1. A contra-angle type operator mechanism for rotatable tools particularly adapted for construction in miniature size comprising, in combination, housing means having a cylindrical bore extending on a first axis, first and second tubular guides in said bore spaced apart collinearly on said first axis with an access space between them, a tool-driver that is rotatable around a second axis passing by but not intersecting said first axis, said tool-driver having extending along said second axis a first set of helical gears which intersects said access space for coupling with a second set of helical gears when said second set of gears is present in said access space rotatably held between said guides and extending along said first axis, said cylindrical bore having at one end an access opening for inserting into and removing from said guides a rotatable tool bearing on its periphery said second set of helical gears, and means in one of said tubuar guides for retaining a rotatable tool in said bore.

2. An operator mechanism according to claim 1 in which the turning ratio between said tool-driver and said second set of gears is in the range between 1:12 and 1:1.

3. An operator mechanism according to claim 1 in which said first axis and said second axis are substantially perpendicular one to the other.

4. An operator mechanism according to claim 3 in which the helix angle of both sets of said helical gears is substantially 45°.

5. An operator mechanism according to claim 1 in which said first axis and second axis are at an angle in the range between perpendicular to one-another and 30 degrees off-perpendicular to one-another.

6. The combination of an operator mechanism according to claim 1 with a tool having a tool shaft bearing on its periphery circumferentially-arrayed gear teeth forming said second set of helical gears, said teeth extending to the end of said shaft which first enters said bore when said tool shaft is inserted into said bore, for meshing said second set of helical gears with said first set of helical gears and for coupling said tool shaft with said tool-driver when said tool shaft is supported in said guides with said second set of helical gears extending between said guides.

7. A combination according to claim 6 in which the helix angle of said second set of gears is in the range from approximately parallel to said first axis to substantially 60 degrees from said first axis.

8. A tool adapted for use with an operator mechanism according to claim 1, said tool having an elongated shaft with an array of helical gear teeth circumferentially arrayed on its outer surface, said teeth having a helix angle between approximately parallel to the axis of said shaft to approximately 60 degrees from said axis, said teeth extending to and at least partially over a first end of the shaft, and a rotationally-working tool affixed to the other end of the shaft.

9. A tool according to claim 8 in which the helix angle of said teeth is substantially 45 degrees.

10. A tool according to claim 8 in which the outer diameter of the helical gear does not exceed approximately 1.6 mm.

11. A tool according to claim 10 in which the diameter of the pitch circle is approximately 1.3 mm.

12. A tool according to claim 10 in which the diameter of the root circle is approximately 1.0 mm.

13. A tool according to claim 8 in which the outer diameter of the helical gear does not exceed approximately 2.30 mm.

14. A contra-angle type operator mechanism according to claim 1 including drive shaft means rotatable around a third axis extending transversely to said first axis, said drive shaft means terminating at one end near said first bore in a drive end that is spaced a distance from said first axis and extending from said drive end away from said first axis, said tool-driver second axis making an obtuse angle with said third axis in a common plane that is traversed by said first axis, said tool-driver having a driven end confronting said drive end of said drive shaft means, connector means between said drive end and said driven end for transmitting rotational motion from said drive-shaft means to said first set of helical gears, second housing means fixed at one end to said first housing means for supporting and enclosing said drive-shaft means and said tool-driver, said first and second housing means forming a single unit having a substantially straight uniform exterior paralleling said third axis.

15. An operator mechanism according to claim 14 in which the turning ratio between said drive shaft and said second set of gears is substantially 1:1.

16. An operator mechanism according to claim 14 in which said first axis traverses said common plane at an angle ranging from 30 degrees forward of perpendicular to 30 degrees aft of perpendicular to said third axis.

17. An operator mechanism according to claim 14 in which said unit housing means is a substantially straight tubular body with transverse exterior dimensions not exceeding approximately five millimeters.

* * * * *